United States Patent [19]
Panzera et al.

[11] Patent Number: 4,828,117
[45] Date of Patent: May 9, 1989

[54] PORCELAIN DENTAL RESTORATION HAVING A PLURALITY OF UNIFORM, COLOR-MATCHED LAYERS

[75] Inventors: Carlino Panzera, Belle Mead; Robert De Luca, Pennington; Robin M. F. Jones, Titusville, all of N.J.

[73] Assignee: Dentsply International Inc., York, Pa.

[21] Appl. No.: 632,154

[22] Filed: Jul. 18, 1984

[51] Int. Cl.$^4$ ............................................. A61C 13/08
[52] U.S. Cl. .............................. 206/63.5; 433/203.1; 433/212.1
[58] Field of Search .................... 206/63.5; 433/203.1, 433/212.1

[56] References Cited

U.S. PATENT DOCUMENTS

| | | | |
|---|---|---|---|
| 3,360,122 | 12/1967 | Ruckert | 206/63.5 |
| 3,932,938 | 1/1976 | Mackta | 433/203.1 |
| 4,294,349 | 10/1981 | Ibsen et al. | 206/63.5 |
| 4,650,418 | 3/1987 | Blair et al. | 433/203.1 |

Primary Examiner—Joseph Man-Fu Moy
Attorney, Agent, or Firm—Charles J. Metz; Edward J. Hanson, Jr.

[57] ABSTRACT

A porcelain dental restoration having a plurality of layers including a translucent porcelain layer overlying a more opaque ceramic layer, wherein the color of each of the said two layers is uniform and wherein the colors of the said two layers match.

7 Claims, 2 Drawing Sheets

PORCELAIN DENTAL RESTORATION HAVING A PLURALITY OF UNIFORM, COLOR-MATCHED LAYERS

The invention relates to porcelain dental restorations such as crowns and bridges having a plurality of uniform, color-matched layers, and to kit for making the same.

BACKGROUND OF THE INVENTION

Metal based porcelain dental restorations such as crowns and bridges comprise a metal framework called a "coping", which is covered by several layers of porcelain to simulate the appearance of natural teeth. The porcelain is applied in a plurality of layers, the first of which is called the "opaque porcelain layer", the purpose of which is to hide the metal framework. The second layer is called the "body porcelain layer". The body porcelain layer exhibits translucence to a degree similar to that of the dentine layer of natural dentition. In addition, there is often a third layer, on top of the body porcelain layer, called the "incisal porcelain layer". The incisal porcelain layer approaches the translucency of the enamel layer of natural dentition. The outer surface is either glazed with a very thin transparent layer, or it is baked to a high gloss.

Color is imparted to a metal-based porcelain dental restoration by coloring the opaque and body porcelain layers. Naturally, it is a major objective in the production of dental restorations to make the restoration resemble as closely as possible the patient's natural teeth.

Recently, all-ceramic dental restorations have been introduced commercially. These restorations replace the metal coping with a ceramic base, and because the metal base is eliminated, they can be made to more closely resemble natural dentition. But even with an all-ceramic restoration, there is obviously still a need to match the color of the patient's natural teeth. One way to color an all-ceramic restoration is to color the ceramic base by any of several techniques (e.g., the color may be incorporated in the base material itself, the base may be stained with a porcelain stain, or the base may be covered with a layer of the desired color called "dentino porcelain"—dentino porcelain is less translucent than body porcelain), and to then add a layer of body porcelain. The body porcelain may be followed by an incisal layer and a glaze, as is the case with metal-based restorations.

Whether the porcelain restoration has a metal base or is all ceramic, its apparent color is influenced by the color of the body porcelain layer and by the color of the layer just beneath the body porcelain. The incisal porcelain and glaze layers contribute little, if anything, to the perceived color of the restoration because they are quite translucent or transparent, and are, at most, only slightly colored. Since natural teeth have translucent layers, i.e., enamel and dentine, the restoration must have translucent layers on its surface to match as closely as possible the appearance of natural teeth. However, the translucency of the body porcelain layer complicates the task of matching the color of natural teeth. The thickness of the body porcelain varies from a rather thick layer at the incisal tip to a thin layer at the gingival end of the restoration. Thus, it is normal for the body porcelain layer thickness to vary from about ½ to 1½ millimeters. Because of this variation in thickness, light penetrates the body porcelain layer to different depths before it is reflected back to the observer, and unless the layer just beneath is exactly the same color as the body porcelain, the apparent color of the restoration will vary over its surface with the thickness of the body porcelain. The reason for this is the following:

Whereas the color of an opaque object is determined by the amount of visible light reflected (from the surface of the object) to the observer by the illuminating light, the perceived color of a porcelain dental restoration is mainly the result of the diffuse reflectance from the translucent body porcelain layer covering an underlying more opaque layer. Perceived color in such a case will be a combination of the reflected color of the translucent layer plus the color reflected from the underlying layer. When the translucent layer varies in thickness, the amount of color contribution from the underlying layer will vary inversely with the thickness of the translucent layer. Therefore, unless the translucent layer and the underlying layer are exactly the same color, the perceived color of the restoration will be dependent upon the thickness of the body porcelain layer.

For the reasons discussed above, it is clear that it is desirable to provide porcelain dental restorations in which the body porcelain matches the color of the layer beneath. Heretofore, however, as far as is known to the inventors herein, there has been no commercial dental porcelain restoration kits in which the body porcelain material, when fired, matched exactly the color of the fired ceramic material of the layer just beneath. In order to compensate for this, the dental technician has often had to apply porcelain stains to different portions of the restoration to prevent the perceived color from varying over its surface to an undesirable degree. This was not only a time consuming task, but also the results were quite dependent upon the skill of the technician.

This invention provides a means for solving the problem discussed above. According to the invention, porcelain can be produced having a predetermined color to match the color of an underlying, more opaque, layer such that the eye cannot discern any difference in color in a composite comprising a layer of the translucent porcelain overlying said underlying layer, even though the translucent porcelain layer varies in thickness.

BRIEF SUMMARY OF THE INVENTION

The invention provides a porcelain dental restoration having a plurality of layers including a translucent layer overlying a more opaque ceramic layer, wherein the color of each of the said two layers is uniform, and wherein the colors of the said two layers match each other.

The invention also provides a kit for the preparation of said porcelain dental restoration.

DEFINITIONS

"Porcelain", as used herein and in the dental restoration arts, refers to the ceramic materials used to cover the base or coping in a restoration such as a crown or bridge. An important function of the porcelain in a dental restoration is to provide the esthetic appearance of natural dentition.

"Ceramic", as used herein, includes the porcelain materials used in a dental restoration, as defined above, and also includes the ceramic base of an all-ceramic dental restoration.

In the dental restoration of the invention, the color-matched layers are both uniform and match each other.

By "uniform" in this sense is meant that the layer has the same color throughout and is free of porcelain stains or the like applied to only a portion of the surface of the layer to compensate for the failure of the two layers to match in color. By "matching in color", as used herein, is meant that when a composite is made having the translucent porcelain layer overlying the more opaque ceramic layer, the eye cannot discern any non-uniformity in the color of the composite even though the thickness of the said translucent procelain layer may vary over the normal range of thicknesses for the body porcelain layer in a porcelain dental restoration (e.g., from about one-half to about one and one-half millimeters). A precise spectrophotometric test, described below, is provided for ascertaining whether or not two ceramic materials of different degrees of translucency have matching colors in the sense intended herein.

DETAILED DESCRIPTION OF THE INVENTION

Figure 1:
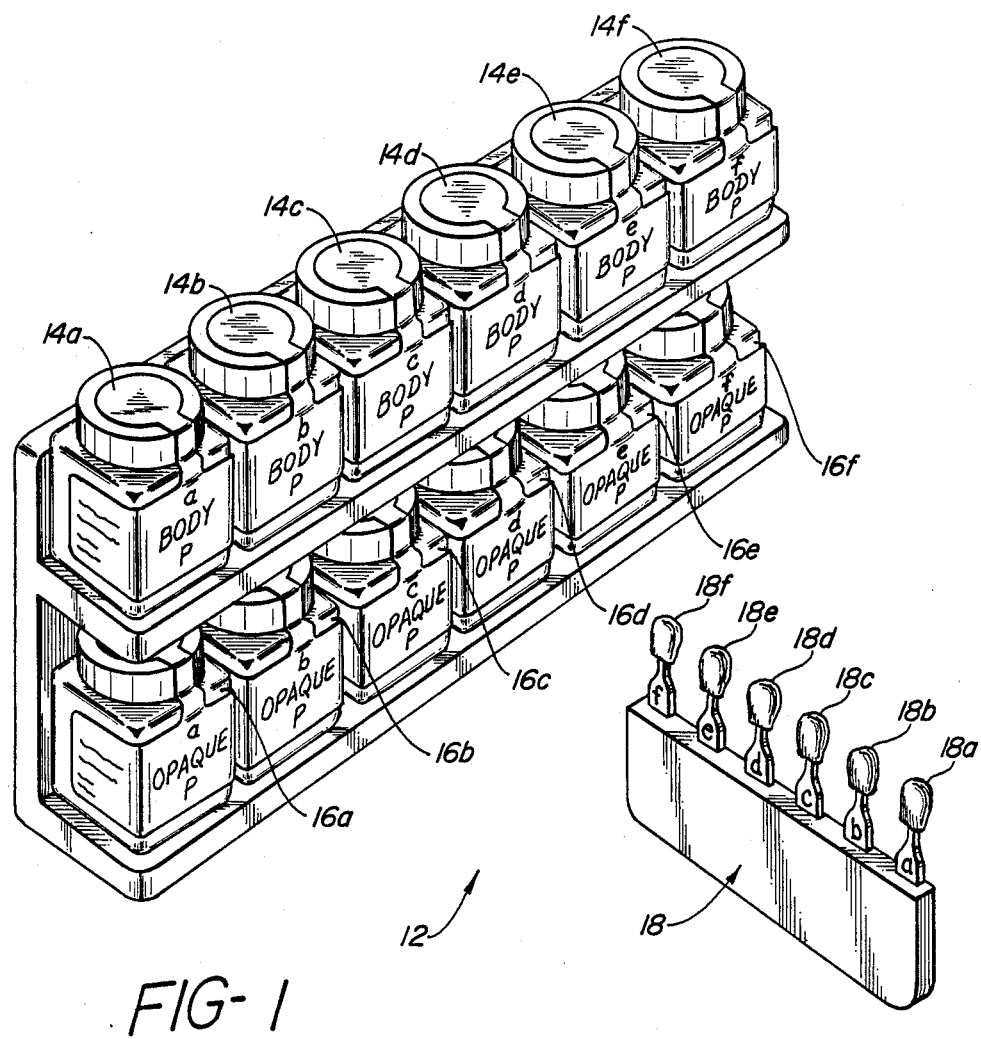
FIG. 1 is a perspective view of a kit provided by this invention, along with a shade guide.

The major contribution of this invention resides in the ability to produce matched pairs of ceramic powder, one being the material for a translucent porcelain and the other being the material for a ceramic having a lesser degree of translucency than said porcelain, such that, when the two powders are fired, the said porcelain and ceramic match in color. The powders provided by the invention may be in the form of dry powders, or they may be premixed with a liquid (usually aqueous based) to form a paste.

In carrying out the invention, first an estimate is made of the nature and proportions of pigments needed to produce a translucent (e.g., body) porcelain of a particular desired color, e.g., to match a shade guide. Disks are pressed from the formulation, and are then fired by standard techniques. The inventors herein have found it convenient to use disks measuring 30 millimeters in diameter by about 3½ millimeters in thickness. The color of the disk is then measured by a spectrophotometer using an opaque, white material (e.g., several thicknesses of white bond paper) as a backing for the disk during the measurement, in order to simulate as closely as practical an infinitely thick disk. (By "infinitely thick disk", as used herein, is meant a disk of a translucent material that is thick enough to prevent light from a spectrophotometer source from being transmitted all the way through the disk. Such transmitted light would be lost, and a false (lower) color value reading would result.) The spectrophotometric analysis is then compared with the analysis of the color that is desired to be matched. If the colors do not match, adjustments are made to the colorants in the porcelain powder, and the process is repeated as many times as is necessary to arrive at the desired color.

This process is repeated for the preparation of the opaque porcelain powder (or for the colored ceramic base material) until a match is found for the body porcelain. A detailed explanation of the method for measuring the color of the fired porcelain or ceramic material follows:

The color analyses were made using a spectrophotometer equipped with a $D_{65}$ standard daylight light illuminant and an 8-inch diameter integrating sphere. (The apparatus was a Hunter model D-535 Spectro-Sensor. A different spectrophotometer can be used, following the principles disclosed herein, but the same instrument should be used for a given series of color comparisons because of the normal variation in accuracy between instruments.) A computer was used to interpret the data, as is more fully explained below. The spectrophotometer settings were small area view (10° visual field), specular included. In operation, white light from the light source hits the sample, some of the light is reflected back, and the reflected light is split into components by a prism or a diffraction grating. Detectors measure the light intensity from 400 nm to 700 nm at intervals of 20 nm ("nm" represents nanometer, or $10^{-9}$ meter), and these readings are compared with the light intensity for that wave length in the source. A commercial computer program, "Chrompac 5," from Applied Color Systems, Princeton, NJ, is used to take the readings and calculate the CIE tristimulus values, X, Y, and Z, of that sample.

The CIE tristimulus values so obtained are then compared with the CIE tristimulus values of the color that is to be matched. This comparision yields a difference in Red-Green and in Blue-Yellow, the vector sum of which is considered to be the chromaticity difference. The difference in color value (light-dark) compared with the color to be matched is also obtained. It has been found that the eye cannot discern a chromaticity difference of about 1.5 or smaller, or a color value difference of about ¾ to 1 or smaller. Therefore, it is desired to match colors such that the chromaticity difference is not greater than about 1.5 and the color value difference is not greater than about 1. For the purposes of this invention, colors meeting this criterion are considered to match.

The principles underlying the utilization of CIE tristimulus values and their calculation from the spectral response of a given color are known to those skilled in the art of color analysis. For instance, see Billmeyer and Saltzman, PRINCIPLES OF COLOR TECHNOLOGY, Second Edition, John Wiley & Sons, 1981, especially pages 44–46, 80–83, and 174, and Judd and Wyszecki, COLOR IN BUSINESS, SCIENCE AND INDUSTRY, Third Edition, John Wiley & Sons, 1975, especially pages 139–169, for discussions of the methods used to calculate CIE tristimulus values. Briefly, the CIE tristimulus values are obtained from the spectrophotometric data by multiplying, wavelength by wavelength, the spectral reflectance of the sample, the relative spectral power of the illuminant, and the values of the respective CIE standard observer functions. These products are then added up for all the wavelengths in the visible region of the spectrum. Tables are available that give the products of the CIE standard observer functions and the spectral power for various CIE illuminants (e.g., daylight, incandescent, and fluorescent) for each wavelength. These tables are, in effect, incorporated in the "Chrompac" 5 computer program referred to above, and are used to calculate the tristimulus values for standard daylight, incandescent, and fluorescent light sources for the sample under evaluation.

The difference in chromaticity and color value between two samples can be calculated from their tristimulus values. The calculations used to obtain the chromaticity difference and color value difference between the sample and the standard were the FMC-2 (Friele, MacAdam, and Chickering) equations that are incorporated in the Chrompac 5 computer program. In the FMC-2 equations, the tristimulus values of the two samples are the input for an algorithm; the output is the chromaticity and color value differences. These equations are the following, in which $\Delta C$ represents the chromaticity difference between the two samples, $\Delta L$ represents the color value (i.e., lightness-darkness) difference between the two samples, $X_s$, $Y_s$, and $Z_s$ represent the tristimulus values for the standard color (i.e., the color against which the sample is being compared), and $X_b$, $Y_b$, and $Z_b$ represent the tristimulus values for the batch (i.e., the sample being compared against the standard):

$$P = 0.724X_s + 0.382Y_s - 0.098Z_s$$

$$Q = -0.48X_s + 1.37Y_s + 0.1276Z_s$$

$$S = 0.686Z_s$$

$$K_1 = 0.55669 + 0.049434Y_s - 0.82575 \times 10^{-3} Y_s^2 + 0.79172 \times 10^{-5} Y_s^3 - 0.30087 \times 10^{-7} Y_s^4$$

$$K_2 = 0.17548 + 0.027556Y_s - 0.57262 \times 10^{-3} Y_s^2 + 0.63893 \times 10^{-5} Y_s^3 - 0.26731 \times 10^{-7} Y_s^4$$

$$A^2 = \frac{0.0000173(P^2 + Q^2)}{1 + \frac{2.73P^2 Q^2}{P^4 + Q^4}}$$

$$B^2 = 0.0003098(S^2 + 0.2015Y_s^2)$$

$$\Delta P = (0.724X_b + 0.382Y_b - 0.098Z_b) - P$$

$$\Delta Q = (-0.48X_b + 1.137Y_b + 0.1276Z_b) - Q$$

$$\Delta S = 0.686Z_b - S$$

$$\Delta L_1 = \frac{(P \cdot \Delta P) + (Q \cdot \Delta Q)}{(P^2 + Q^2)^{\frac{1}{2}}}$$

$$\Delta L_2 = \frac{0.279(\Delta L_1)}{A}$$

$$\Delta L = K_2 (\Delta L_2)$$

$$\Delta CRG_1 = \frac{(Q \cdot \Delta P - P \cdot \Delta Q)}{(P^2 + Q^2)^{\frac{1}{2}}}$$

$$\Delta CRG_2 = \frac{\Delta CRG_1}{A}$$

$$\Delta CRG_3 = \Delta CRG_2 (K_1)$$

$$\Delta CYB_1 = \frac{S \cdot \Delta L_1}{(P^2 + Q^2)^{\frac{1}{2}}}$$

$$\Delta CYB_2 = \frac{\Delta CYB_1}{B}$$

$$\Delta CYB_3 = \Delta CYB_2 (K_1)$$

$$\Delta C_1 = [(\Delta CRG_3)^2 + (\Delta CYB_3)^2]^{\frac{1}{2}}$$

$$\Delta C = K_1 \cdot \Delta C_1$$

EXAMPLE 1

In this example, a translucent body porcelain was prepared having a predetermined color to match a shade guide, and an opaque porcelain was prepared to match it.

The translucent body porcelain in this Example 1 had the following composition, prior to addition of pigments (all proportions given in this Example are parts by weight):

TABLE I

| | |
|---|---|
| $SiO_2$ | 65.5 |
| $Al_2O_3$ | 15 |
| $K_2O$ | 12.5 |
| $Na_2O$ | 2.67 |
| $Li_2O$ | 1.25 |
| CaO | 2 |
| $SnO_2$ | 0.2 |

The pigmented body porcelain formulation is presented below in Table II. The pigments shown in Table II and the other tables are identified by their commercial trade names, by which they are available. Their exact compositions are not revealed by their manufacturers.

TABLE II

| | |
|---|---|
| Body Porcelain | 99.6116 |
| Yellow Y36 | 0.2268 |
| Pink 15M345 | 0.1332 |
| Gray 4A9391(D)[1] | 0.0284 |

[1] In this formulation, the commercially obtained Gray 4A9391 was diluted "(D)" with 4 parts by weight of glass to 1 part of pigment.

The sample preparation technique was the following:

The unshaded body porcelain powder produced as described earlier in this specification plus the pigments were mixed for 30 minutes using an automatic mortar and pestle. Body porcelain disks were made by pressing 7.0 grams of body porcelain powder in a circular die measuring 1.5 inches in diameter, using 10,000 pounds of load. The disk was fired by placing it in a Transi Vac dental furnace at 1200° F. The furnace chamber was evacuated to 29 inches of mercury (to ensure removal of all entrapped air from the disk), and the temperature was increased to 1700° F. at the rate of 90° to 100° F./minute. The furnace chamber was brought back to atmospheric pressure and the furnace temperature was increased to 1800° F. at the same rate. The sample was removed from the hot chamber and allowed to cool down to ambient temperature. It measured 30 millimeters in diameter by 3½ millimeters thick.

The opaque sample (whose formulation is given below, after Table IV) was made by pressing 2.5 grams of opaque powder formulation in a one-inch die. The pressing and firing was the same as the body porcelain, except that the top temperature was 1840° F. The sample measured 19 millimeters in diameter by 3 millimeters thick.

The body porcelain disks were analyzed spectrophometrically, using several (e.g., six) thicknesses of white bond paper as a backing. The particular bond paper used had the following spectral response on the spectrophotometer:

TABLE III

| nm | % Reflectance |
|---|---|
| 400 | 43.51 |
| 420 | 79.71 |
| 440 | 89.47 |
| 460 | 89.19 |
| 480 | 89.80 |
| 500 | 90.55 |
| 520 | 91.04 |
| 540 | 91.26 |
| 560 | 91.42 |
| 580 | 91.72 |
| 600 | 92.17 |
| 620 | 92.97 |

TABLE III-continued

| nm | % Reflectance |
| --- | --- |
| 640 | 93.77 |
| 660 | 94.47 |
| 680 | 95.01 |
| 700 | 95.28 |

The spectrophotometric response of the body porcelain sample was the following:

TABLE IV

| nm | % Reflectance |
| --- | --- |
| 400 | 17.9 |
| 420 | 21.5 |
| 440 | 25.0 |
| 460 | 28.7 |
| 480 | 32.4 |
| 500 | 36.4 |
| 520 | 39.2 |
| 540 | 41.5 |
| 560 | 45.4 |
| 580 | 49.3 |
| 600 | 51.2 |
| 620 | 52.4 |
| 640 | 53.2 |
| 660 | 53.8 |
| 680 | 54.4 |
| 700 | 54.8 |

The opaque porcelain was made by adding 17.5 parts, by weight, of stannic oxide opacifier to 82.5 parts, by weight, of the translucent body porcelain described above. A first approximation to match the color of the body porcelain was made from the following formulation:

TABLE V

| Opaque porcelain | 92.4787 |
| --- | --- |
| Yellow Y36 | 6.8300 |
| Gray A49391 | 0.1854 |
| Brown 2B9075 | 0.5059 |

The sample disk was made from the opaque porcelain by the sample preparation technique described above, and it was analyzed spectrophotometrically, with the following results:

TABLE VI

| nm | % Reflectance |
| --- | --- |
| 400 | 18.4 |
| 420 | 21.2 |
| 440 | 24.1 |
| 460 | 27.3 |
| 480 | 30.5 |
| 500 | 34.4 |
| 520 | 38.4 |
| 540 | 41.8 |
| 560 | 44.8 |
| 580 | 47.7 |
| 600 | 50.2 |
| 620 | 53.0 |
| 640 | 54.9 |
| 660 | 55.7 |
| 680 | 56.2 |
| 700 | 57.1 |

The spectral response of this opaque porcelain was compared with that of the body porcelain that is desired to be matched, using the FMC-2 equations described above, with the following results:

TABLE VII

| $\Delta L$ | $\Delta CRG$ Ill. | $\Delta CYB$ $K_1$ | $K_1$ | $\Delta C$ |
| --- | --- | --- | --- | --- |
| D | 3.3 | 1.8 | 3.7 | −1.1 |
| A | 3.1 | 1.0 | 3.3 | −0.7 |
| F | 1.3 | 1.2 | 1.7 | −1.2 |

In the table, "ILL." stands for type of illumination, "D", "A", and "F" stand for, respectively, daylight, incandescent (tungsten), and fluorescent, $\Delta CRG$ and $\Delta CYB$ represent, respectively, the color differences along the red-green and yellow-blue axes, $\Delta C$ represents the chromaticity difference, and $\Delta L$ represents the color value difference. (Even though the spectrophotometer uses a daylight ($D_{65}$) source, the tristimulus values for each color under daylight, incandescent, and fluorescent illumination are calculated by the computer, since the spectral power for each of these illuminants is known and is incorporated in the algorithm used to calculate the tristimulus values.)

As can be seen from the data presented in Table VII, the chromaticity difference ($\Delta C$) is greater than 1.5 and the color value difference ($\Delta L$) is greater than 1, so the colors did not match closely enough to be considered to be a color match.

The pigmented formulation was modified so as to give the following formulation:

TABLE VIII

| Opaque porcelain | 92.9660 |
| --- | --- |
| Yellow Y36 | 6.3732 |
| Gray A49391 | 0.2186 |
| Brown 2B9075 | 0.4423 |

The spectral response of a disk made from this opaque powder was as indicated below. It is compared with the spectral response obtained from a second analysis of the body porcelain disk described above. The second analysis differs slightly from the spectral response set forth above in Table IV, but is within the precision of the technique.

TABLE IX

| | % Reflectance | |
| --- | --- | --- |
| nm | Body Porcelain | Opaque Porcelain |
| 400 | 18.8 | 20.0 |
| 420 | 21.7 | 22.2 |
| 440 | 25.1 | 25.1 |
| 460 | 28.9 | 28.3 |
| 480 | 32.6 | 31.5 |
| 500 | 36.6 | 35.3 |
| 520 | 39.4 | 39.1 |
| 540 | 41.8 | 42.5 |
| 560 | 45.8 | 45.4 |
| 580 | 49.8 | 48.2 |
| 600 | 51.9 | 50.6 |
| 620 | 53.2 | 53.1 |
| 640 | 54.0 | 54.7 |
| 660 | 54.7 | 55.5 |
| 680 | 55.4 | 55.9 |
| 700 | 56.1 | 56.8 |

The FMC-2 equations were used to compare these two spectral responses, with the following results:

TABLE X

| Ill | $\Delta CRG$ $K_1$ | $\Delta CYB$ $K_1$ | $\Delta C$ | $\Delta L$ |
| --- | --- | --- | --- | --- |
| D | 0.2 | 0.1 | 0.2 | −0.9 |
| A | 0.3 | 0.2 | 0.4 | −0.8 |

TABLE X-continued

| III | ΔCRG K₁ | ΔCYB K₁ | ΔC | ΔL |
|---|---|---|---|---|
| F | −0.9 | −0.2 | 0.9 | −1.0 |

Since the chromaticity difference (ΔC) was 1.5 or less and the color value difference (ΔL) was 1 or less, the colors of these two porcelains were considered to match. When a dental restorative is made utilizing a layer of this body porcelain varying in thickness from ½ to 1½ millimeters, overlying a layer of this opaque porcelain, the naked eye is unable to perceive any non-uniformity in color over the surface of the restoration, no matter what the thickness of the body porcelain layer.

It is noted that in Table X, the color value difference was a negative number. This means that the opaque porcelain was slightly darker than the body porcelain. However, since the color value difference was less than 1 (as an absolute value), the requirement of this invention is met.

A visual comparision of the body porcelain and opaque porcelain disks that matched as defined herein reveals a rather startling fact. They look quite different, because of their differences in degree of opacity. It has been the experience of the inventors herein that many dental technicians do not believe that body porcelain and opaque porcelain disks that match as defined herein are, in fact, the same color, until a sample dental restoration is made using the two porcelains. It is then seen that the color of the restoration is independent of the thickness of the body porcelain layer. This difference in visual appearance between body porcelain and opaque porcelain disks that match may very well account for the fact that, until now, there have been no commercial matched pairs of porcelain materials for dental restorations that matched, as defined herein.

The invention is useful in providing color-matched pairs of porcelain materials of different degrees of translucence. The translucence of a porcelain sample may be measured using a densitometer to measure the amount of reflected light. The sample should be backed by a black material (i.e., a material that has not more than about 4% reflectance). Using sample disks 3½ millimeters thick (except for opaque samples, for which the thickness is not relevant), the following amounts of reflectance are found for different types of porcelain:

TABLE XI

| Porcelain Type | % Reflectance |
|---|---|
| Incisal | 14–24 |
| Body | 35–45 |
| Dentino | 70–80 |
| Opaque | 100 |
| Glaze | Below 10, typically 3–5 |

FIG. 1 shows a kit as provided by the invention. The kit, shown generally as 12, contains bottles 14a–f of body porcelain powder, bottles 16a–f of opaque porcelain powder, and a shade guide 18. The individual model teeth in the shade guide 18 are labeled 18a–f. The colors of the fired porcelain made from the labeled bottles 14a–f of body porcelain powder match the colors of the fired porcelain made from the correspondingly labeled bottles 16a–f of opaque porcelain powder. Both fired porcelain colors also match the colors of the correspondingly labeled model teeth 18a–f in the shade guide 18.

When a dental restoration is made utilizing correspondingly labeled body and opaque porcelain powders from this kit 12, the apparent color (i.e., the color that can be discerned by the naked eye) of the restoration is independent of the thickness of the body porcelain layer that overlies the opaque porcelain layer.

Figure 2:
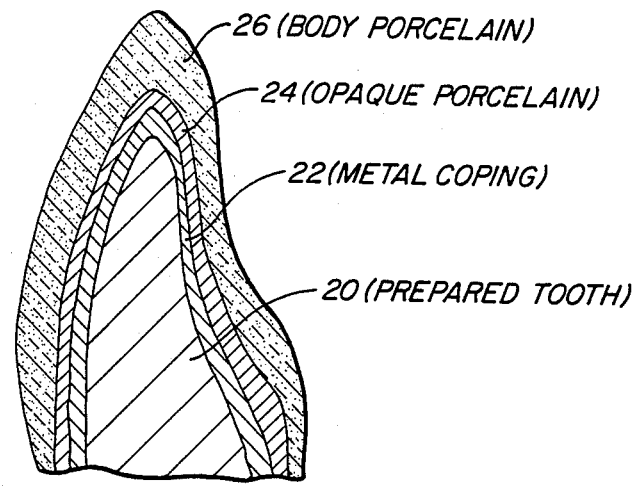
FIGS. 2 and 3 are cross-sectional elevations of dental restorations provided by the invention.
Figure 3:
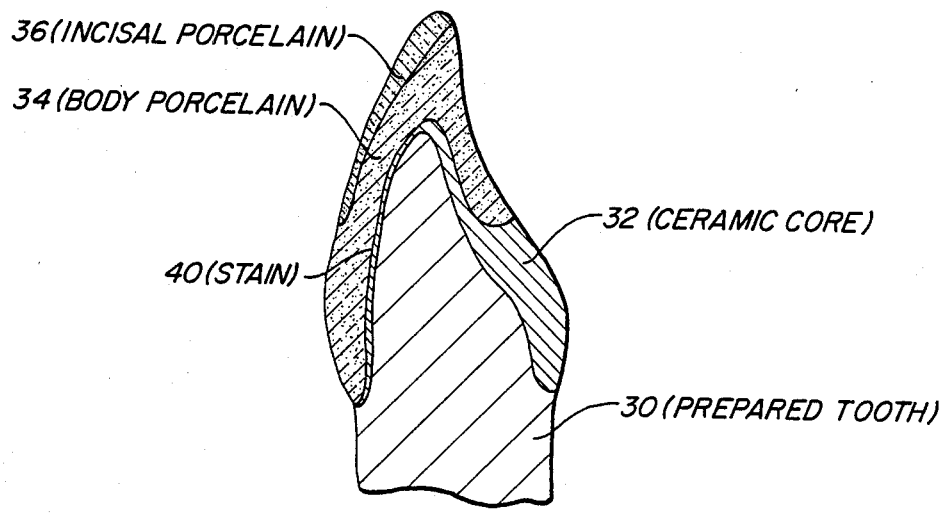

FIGS. 2 and 3 illustrate dental restorations made in accordance with the invention.

In FIG. 2, a metal-based porcelain dental restoration is shown mounted in place on a prepared tooth 20. The restoration includes a metal coping 22, which is covered with a layer of opaque porcelain 24, which in turn is covered with a layer of body porcelain 26. Optionally, the body porcelain 26 may be covered with a layer of incisal porcelain and/or a glaze, not shown. In FIG. 3, an all ceramic restoration is shown. This restoration includes a ceramic core 32, which fits over the prepared tooth 30. The ceramic core 32 is completely covered with a porcelain stain 40. A layer of body porcelain 34 overlies the stained ceramic core 32, and a veneer or incisal porcelain 36 is included at the incisal tip of the restoration.

The ceramic materials employed in the invention can be the conventional glass ceramic powder materials that are used in the preparation of dental restorations. One typical preferred porcelain powder useful for metal based restorations is composed of the following basic components (prior to addition of pigments):

| Component | Parts, by weight | |
|---|---|---|
| | Broad | Preferred |
| $SiO_2$ | 65.5 ± 4 | 65.5 ± 1 |
| $Al_2O_3$ | 15 ± 2 | 15 ± 1 |
| $K_2O$ | 12.5 −1, +2 | 12.5 ± 1 |
| Flux | 4 ± 1 | 4 ± 1 |
| MO | 2 ± 1 | 2 ± 0.5 |
| Opacifier | 0.2 ± 0.1 or 24 ± 3 | 0.2 ± 0.1 or 24 ± 3 |

In the foregoing table, "flux" represents either sodium oxide or lithium oxide, or a mixture thereof, and optionally, boron oxide, and M represents either calcium or magnesium or a mixture thereof. In the formulation, the opacifier can be tin oxide or titanium dioxide. The version containing 24±3 parts of opacifier is useful as an opaque porcelain for metal-based restorations, and the version containing 0.2±0.1 part of opacifier is useful as a body porcelain.

The porcelain material can be made by making a mixture of the powdered metal oxides (the opacifier is usually added later, when the colorants are added), in the proportions mentioned above, or a mineral such as feldspar or nepheline syenite can be mixed with the appropriate metal oxides to make up the above-stated composition. The alkali metal oxides and alkaline earth metal oxides are most convenient to use in the form of their carbonates. In one preferred aspect, the flux is composed of sodium oxide in amounts of $2\frac{2}{3} \pm \frac{1}{3}$ weight per cent, and lithium oxide in amounts of $1\frac{1}{4} \pm \frac{1}{4}$ weight per cent. As is known in the art, boron oxide tends to lower the coefficient of thermal expansion. This should be taken into account if it is to be used, and correspondingly more sodium oxide may need to be used in the flux to raise the coefficient of thermal expansion so that it will closely match that of the metal coping.

The components of the porcelain are blended, preferably reduced to a very fine powder as by ball milling for 1 to 3 hours, and then fused to form a glass. The fusion can be carried out at 1300° C. ±100° C. for from about 1 to 4 hours. After the fusion, the material is quenched in water, and then reheated to elevated temperature (for instance, 1000° C. ±50° C.) for from about 1 to about 6 hours to permit the crystalline phase (that is, leucite) to form and grow. After the desired amount of crystalline material has formed, the material is quenched, crushed, and reduced to a fine powder as by ball milling for from 1 to 3 hours. The usual pigments, such as chromates, vanadates, oxides, and manganates of iron, cobalt, nickel, zirconium, vanadium, or praseodymium, can be added to the porcelain powder in small amounts after the ball milling, as is illustrated below in the Examples. Preferably, the powder is fine enough to pass through a 160 to 170 mesh screen (Tyler Sieve Series). After the porcelain powders have been prepared, they are then employed in making a dental restoration in the conventional manner. This conventional manner is outlined as follows:

The general technique for the construction of a metal-based porcelain-coated dental restoration such as a crown or bridge is the following: first, an impression is taken of the denture area that has been prepared to receive the restoration. A die is prepared from the impression, and a metal base is cast to fit this die. The metal base or coping has an internal shape to match exactly the prepared dentition. The porcelain powder is then mixed with water to form a slurry, which is then applied to the metal base by standard procedures. (This first porcelain powder is the opaque porcelain powder.) The slurry is coated uniformly on the form of the finished crown or multiple unit bridge. It is then dried, usually fired in vacuum in an electric furnace to the desired firing temperature. The body porcelain powder is similarly formed into a slurry, is applied to the restoration in the form of the dentine layer of natural dentition, and is then fired, as above. The incisal layer and glaze, if used, are applied in a similar manner.

The invention is also applicable to all-ceramic dental restorations. The ceramic core that has an internal shape to match exactly the prepared dentition (i.e., the ceramic "equivalent" of a metal coping) can be produced by the procedure described by Starling et al., U.S. Pat. No. 4,265,669, Riley et al., European Patent Application No. 30,850, published on June 24, 1981, and Stephan et al., U.S. Pat. No. 4,374,076. Briefly, the ceramic material used as a core, when fired, comprises a substantially nonporous and shrink-free ceramic body containing a major amount of crystalline material with the remainder being interstitial glass. The crystalline material contains aluminum oxide and magnesium aluminate spinel. It is made from a raw batch containing alumina, magnesia, glass, and a silicone resin binder which decomposes during firing to leave a residue of silica. The alumina and magnesia combine to form spinel during the firing. The spinel expands during its formation to compensate for the shrinkage that would otherwise occur from the formation of the fired ceramic from the raw batch.

The ceramic core may be colored by adding pigments to the core formulation. Alternatively, a porcelain stain can be used as a thin coating to color the core. Such a stain comprises a very thin layer of a glaze or glass containing pigments. In this case, the glaze acts as a carrier or a binder for the pigments. The porcelain stain is applied uniformly over the entire surface of the core. A third way to color the entire core is to coat the core with a uniform layer of pigmented dentino porcelain. Dentino porcelain may be made by a number of different procedures. One way is to mix about three parts by weight of colored core ceramic material with one part by weight of colored body porcelain. (It is interesting to note that a dentino porcelain made this way will have a different spectrophotometric color than the body porcelain material from which it is made because of the contribution to the total color that is made by the opaque materials in the core ceramic powder.) Another way to make dentino porcelain is to add more opacifier, such as alumina, zirconium silicate, or the like, to body porcelain.

The preparation of such colored ceramic cores is known in the art, and need not be explained here in greater detail. The following formulations illustrate compositions that can be used in the above-said three procedures to make a colored ceramic core:

One preferred formulation for a pigmented shrink-free ceramic core material is the following:

|  | Parts, by Weight |
| --- | --- |
| $Al_2O_3$ | 140 |
| $BaO$—$SiO_2$—$Al_2O_3$ Glass (53% BaO; 42% $SiO_2$; 5% $Al_2O_3$) | 30 |
| MgO | 20 |
| Edgar Plastic Kaolin | 9 |
| Calcium Stearate | 2 |
| Acrawax C (Stearyl Amide Wax-mp 290° F.) | 2 |
| Silicone resin (General Electric SR350) | 28 |
| Pigments | about 12 to 20 |

A porcelain stain that can be used as a coating on an unpigmented ceramic core is illustrated by the following formulation:

|  | Parts, by Weight |
| --- | --- |
| $K_2O$ | 0.3 |
| $Na_2O$ | 5.9 |
| CaO | 0.8 |
| $B_2O_3$ | 9.2 |
| $Al_2O_3$ | 10.7 |
| $SiO_2$ | 72.7 |
| SrO | 0.15 |
| BaO | 0.8 |
| Pigment | 1 ± ¼ |

A typical pigmented dentino porcelain formulation, which can be used as a layer on an unpigmented ceramic core, has the following formulation:

|  | Parts, by Weight |
| --- | --- |
| $K_2O$ | 4 |
| $Na_2O$ | 4.5 |
| CaO | 2.7 |
| $B_2O_3$ | 7.9 |
| $Al_2O_3$ | 9.4 |
| $SiO_2$ | 71.5 |
| Opacifier | 10 ± 5 |
| Pigments | 1 ± 0.5 |

The translucent body porcelain layer is coated on the ceramic base as the next layer, by a procedure analogous to the procedure outlined above for metal-based restorations. A typical body porcelain suitable for use with an all ceramic restoration would have the same formulation as the dentino porcelain, with the opacifier being reduced to about 0.2 part.

What is claimed is:

1. A kit for the preparation of porcelain dental restorations having a layer of translucent porcelain overlying a more opaque ceramic layer, said kit comprising at least one labeled container of colored translucent porcelain powder and at least one labeled container of ceramic material for said more opaque layer, wherein when the correspondingly labeled translucent porcelain powder and ceramic material for said more opaque layer are fired, the colors of said translucent porcelain and said more opaque ceramic layer match spectrophotometrically such that the chromaticity difference between the two colors is not greater than 1.5, and the color value difference between the two colors is not greater than 1, calculated by the FMC-2 equations from the CIE tristimulus values of the two colors for standard daylight, incandescent, and fluorescent illumination.

2. The kit of claim 1 including a plurality of pairs of containers of labeled translucent porcelain powder and correspondingly labeled containers of ceramic material for said more opaque layer.

3. The kit of claim 1 wherein the said colored translucent porcelain powder is a body porcelain powder that, when fired, has a reflectance of about 35 to 45 per cent, measured by a densitometer using a sample about three and one-half millimeters thick backed by a black material.

4. The kit of claim 3 wherein said ceramic material for said more opaque layer is a ceramic powder that, when fired, is opaque.

5. The kit of claim 3 wherein said ceramic material for said more opaque layer is a dentino porcelain powder that, when fired, has a reflectance of about 70 to 80 per cent, measured by a densitometer using a sample about three and one-half millimeters thick backed by a black material.

6. The kit of claim 3 wherein said ceramic material for said more opaque layer comprises powder from which to make a ceramic core for a dental restoration.

7. The kit of claim 6 wherein said ceramic material for said more opaque layer additionally includes a porcelain stain.

* * * * *